(12) United States Patent
Zarembinski

(10) Patent No.: US 7,631,814 B2
(45) Date of Patent: Dec. 15, 2009

(54) PORTABLE SPORTS EQUIPMENT SCENT DISPERSION APPARATUS

(76) Inventor: Thomas P. Zarembinski, 750 Pennington Pl., Vadnais Heights, MN (US) 55127

( * ) Notice: Subject to any disclaimer, the term of this patent is extended or adjusted under 35 U.S.C. 154(b) by 98 days.

(21) Appl. No.: 11/483,812

(22) Filed: Jul. 10, 2006

(65) Prior Publication Data

US 2007/0207067 A1    Sep. 6, 2007

(51) Int. Cl.
*A61L 9/04* (2006.01)
*A61L 9/12* (2006.01)
(52) U.S. Cl. .................. 239/55; 239/53; 239/58
(58) Field of Classification Search .......... 239/34, 239/36, 44, 53–59, 152, 154, 600
See application file for complete search history.

(56) References Cited

U.S. PATENT DOCUMENTS

| 4,944,455 A | * | 7/1990 | Haust et al. .................. 239/59 |
| D345,788 S | | 4/1994 | Green |
| 5,555,640 A | | 9/1996 | Ou |
| 5,755,040 A | | 5/1998 | Ou |
| D398,976 S | | 9/1998 | Green |
| D399,945 S | | 10/1998 | Bonomo et al. |
| 5,930,915 A | | 8/1999 | Dhaemers |
| 6,018,885 A | | 2/2000 | Hill |
| 6,103,201 A | | 8/2000 | Green |
| 2007/0001023 A1 | * | 1/2007 | Green et al. ............ 239/34 |

OTHER PUBLICATIONS

Tinks Scent Bombs 3 pk—internet ad eders.com, 2006.
Dennis Green, LTD Scented Sneaker Balls, Product Insert.

* cited by examiner

*Primary Examiner*—Darren W Gorman
(74) *Attorney, Agent, or Firm*—Sherrill Law Offices, PLLC; Janet P. Schafer

(57) ABSTRACT

An apparatus and method for dispensing air freshening odors for enhancing the drying and deodorizing of clothing and sporting equipment not easily laundered. A two-piece housing forms spherical structure retaining a aromatic element inside. Dispensing of the air freshening odors is activated by the air flow past the aromatic element for masking and neutralizing odors. The two-piece housing having a top portion and a bottom portion, each hemispherical shaped and interconnected to permit the bottom portion to be rotated relative to the top portion, opening and closing an orifice controlling the amount of scent released.

3 Claims, 15 Drawing Sheets

__US 7,631,814 B2__

PORTABLE SPORTS EQUIPMENT SCENT DISPERSION APPARATUS

BACKGROUND

The present invention is directed generally to air freshener apparatus. In particular, the present invention relates to a portable sports equipment scent dispersing apparatus having an air freshener dispenser of generally spherical shape. The spherical shape aids in facilitating dispersion of odor neutralizing scent and deodorizing of sports equipment, including clothing articles, in an existing sports equipment bag, closet, locker and the like and having a means for controlling the amount of scent dispensed, adaptable for use in hunting situations.

Sporting equipment that cannot be easily laundered, such as skates, helmets, pads and the like, may become offensively odiferous with repeated wearing. Keeping sporting equipment dry and odor free is one of the main difficulties associated with many sporting or recreational activities. Equipment bags trap in moisture which makes them an ideal breeding ground for bacteria, mold, mildew and fungus. These contaminants are the real culprit behind equipment odor and in addition to being unpleasant, they pose a variety of health risks.

Several US patents describe drying chambers for use to dry clothing or the like. Examples of such devices are the Hill U.S. Pat. No. 6,018,885, the Ou U.S. Pat. No. 5,755,040 and U.S. Pat. No. 5,555,640.

SUMMARY

The present invention provides a portable sports equipment scent dispersing apparatus having an air freshener dispenser of generally spherical shape. The air freshener dispenser is constructed of two hemispherical shaped portions, a top portion and a bottom portion, which when positioned together forms a sphere. The bottom portion turns relative to the top portion. The portable air freshener dispenser dispenses odor neutralizing and deodorizing scent for use with clothing articles in any existing locker, closet, sports equipment bag, including home storage. The air freshener dispenser utilizes oil based compounds to neutralize and deodorize sports equipment and has means for controlling the amount of scent dispensed. The air freshener dispenser also can be adapted for use in hunting situations.

BRIEF DESCRIPTION OF THE DRAWINGS

Understanding of the invention will be enhanced by referring to the accompanying drawings, in which like numbers refer to like parts in the several views and in which.

DETAILED DESCRIPTION OF THE CURRENTLY PREFERRED EMBODIMENTS

Figure 1:
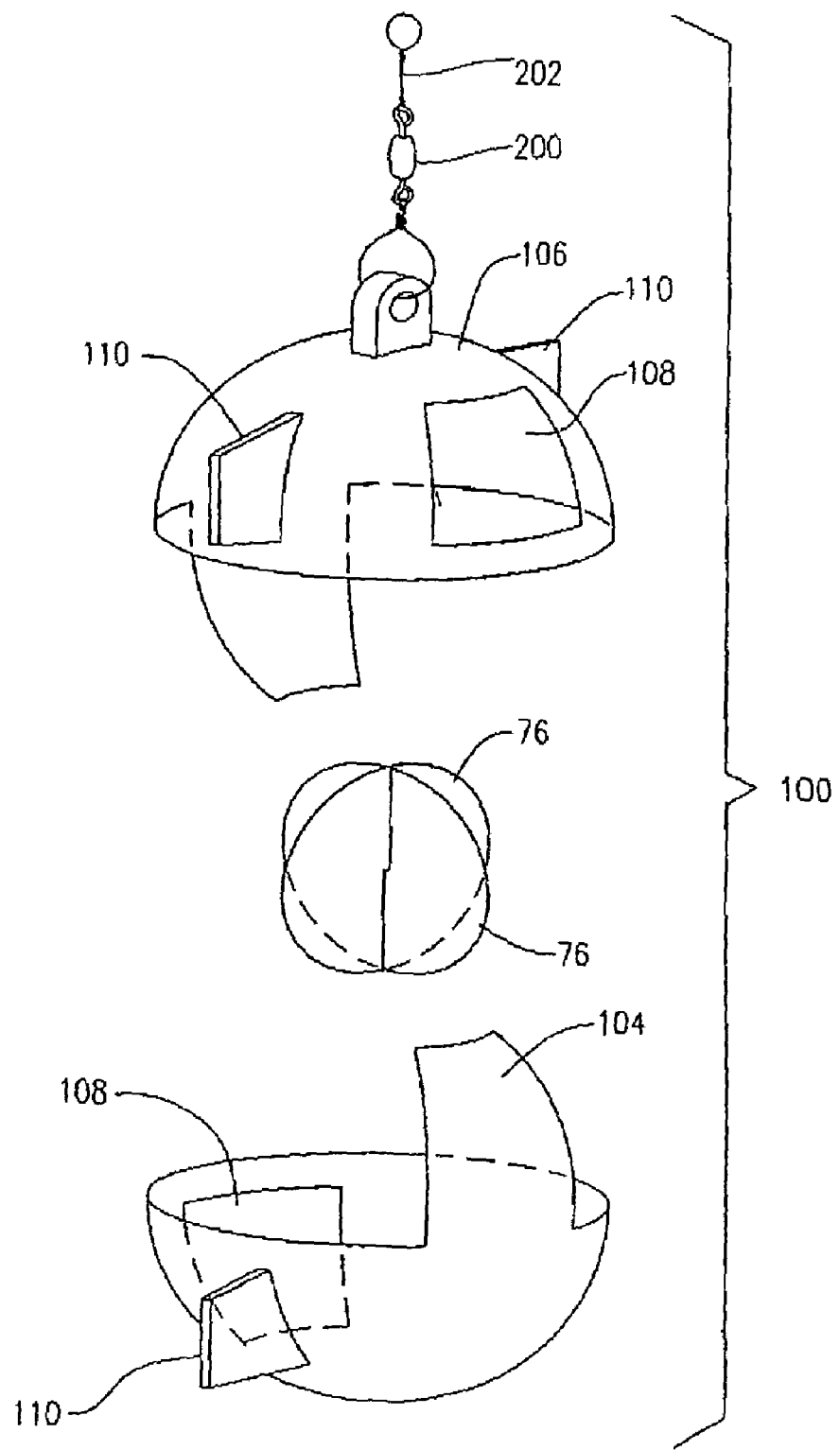
FIG. 1 is a perspective exploded detail view of parts comprising an aromatic structure.

A portable air freshener dispenser apparatus, generally indicated at 100 in FIG. 1, is used for dispensing odor neutralizing and fragrancing scent which enhances deodorizing of clothing and sporting equipment not easily laundered for use in an equipment bag, locker, closet or the like. An air freshener dispenser apparatus 100, formed of two hemispherical portions which, when positioned together, form a generally spherical shape with adjustable vents 114 shown at FIG. 2 while the bottom portion turns relative to the top portion to open, or close or partially open an outlet vent. The aromatic element 76, a pair of aromatic discs positioned together and placed for use within the air freshener dispenser apparatus 100, are made of a special fiber element that is impregnated with compounds of selected natural oils. The natural oil compounds act as an odor neutralizer which rely on convection to release the neutralizing dry vapor into the air. A gentle air-flow, which is naturally generated by the movement of the aromatic element 76 within the vented sphere-shaped air freshener dispenser apparatus 100, releases the vapor to the odor source, neutralizing the odor.

The air freshening dispenser apparatus 100 has a two-piece housing 106, 104, and a aromatic element 76 activated by the air flow, for neutralizing odors. Means are provided to control the amount of scent dispensed. These means include inlet vents with a vent control and a gate which may be used to cover partially or completely orifices 108 formed in the sidewalls of the spherical container. Means are also provided to attach the top portion 106 to the bottom portion 104 forming the sphere 102. A suspension chain 202 with a swivel 200 is provided for hanging the air freshener dispenser apparatus 110 from a hook or other structure.

FIG. 1 is a perspective exploded detail view of parts comprising a two piece structure that, when snapped together, forms a sphere-shaped aromatic structure or air freshener dispenser apparatus 100 where the aromatic element 76, is positioned inside the two-piece sphere-shaped air freshener dispenser apparatus 100.

The spherical air freshener dispenser apparatus 100 provides housing to a pair of aromatic discs 76 that are each slit to the center such that they fit perpendicularly relative to each other and rotate within the spherical air freshener dispenser apparatus 100. Spherical air freshener dispenser apparatus 100 may be hung within locker 73 or other container or it may be permitted to roll around within, for example an sports bag. Also, spherical air freshener dispenser apparatus 100 may be used with hunting scent as a lure for wild animals, FIGS. 13 & 14. Ambient air movement pushes the wings 110 of the hanging air freshener dispenser apparatus 100 causing the air freshener dispenser apparatus 100 to spin about the swivel 200 on its suspension chain 202 movement of air across the aromatic element 76 releases the scent.

Figure 2:
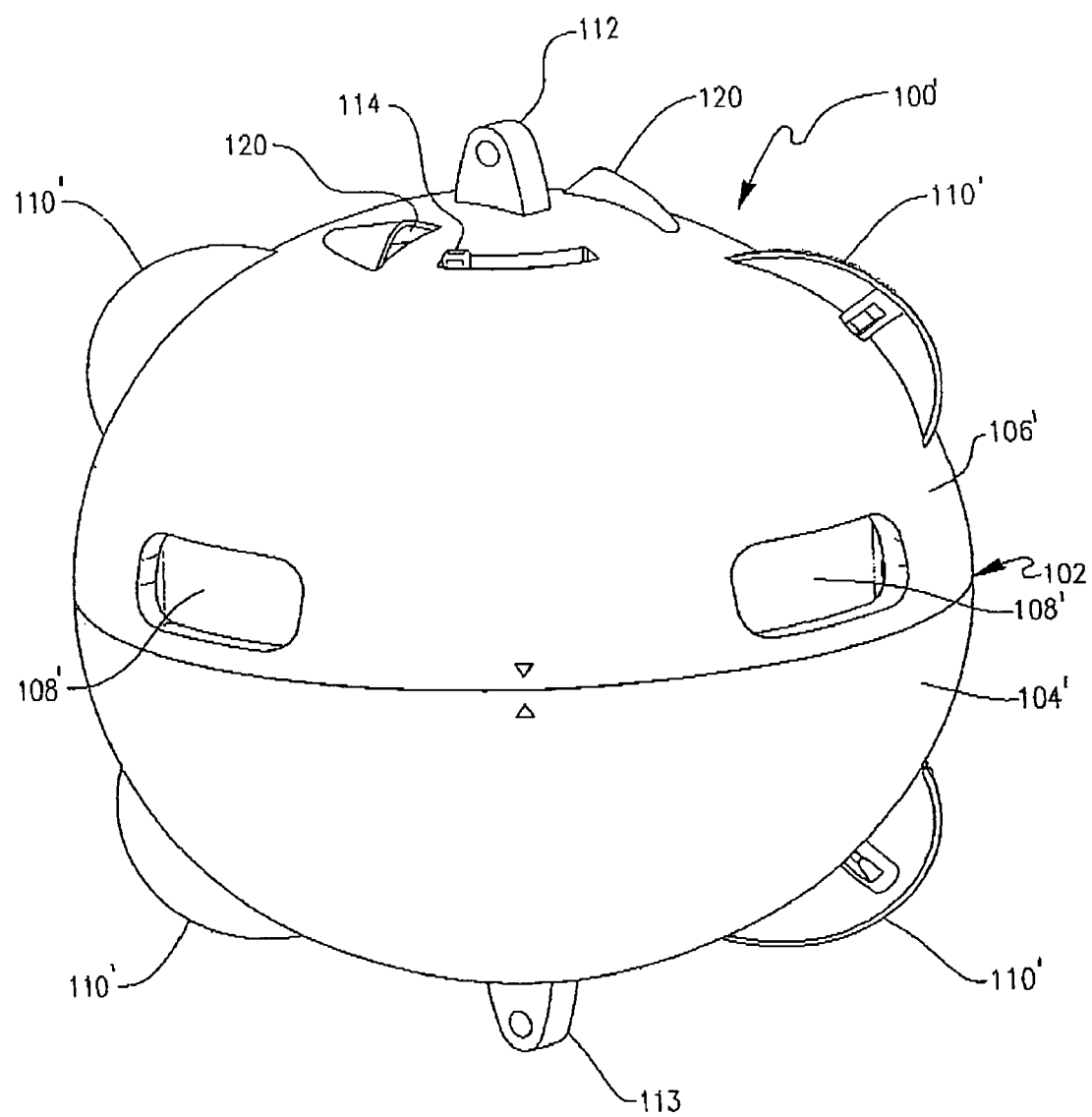
FIG. 2 is a perspective view of the preferred form of the invention.
Figure 3:
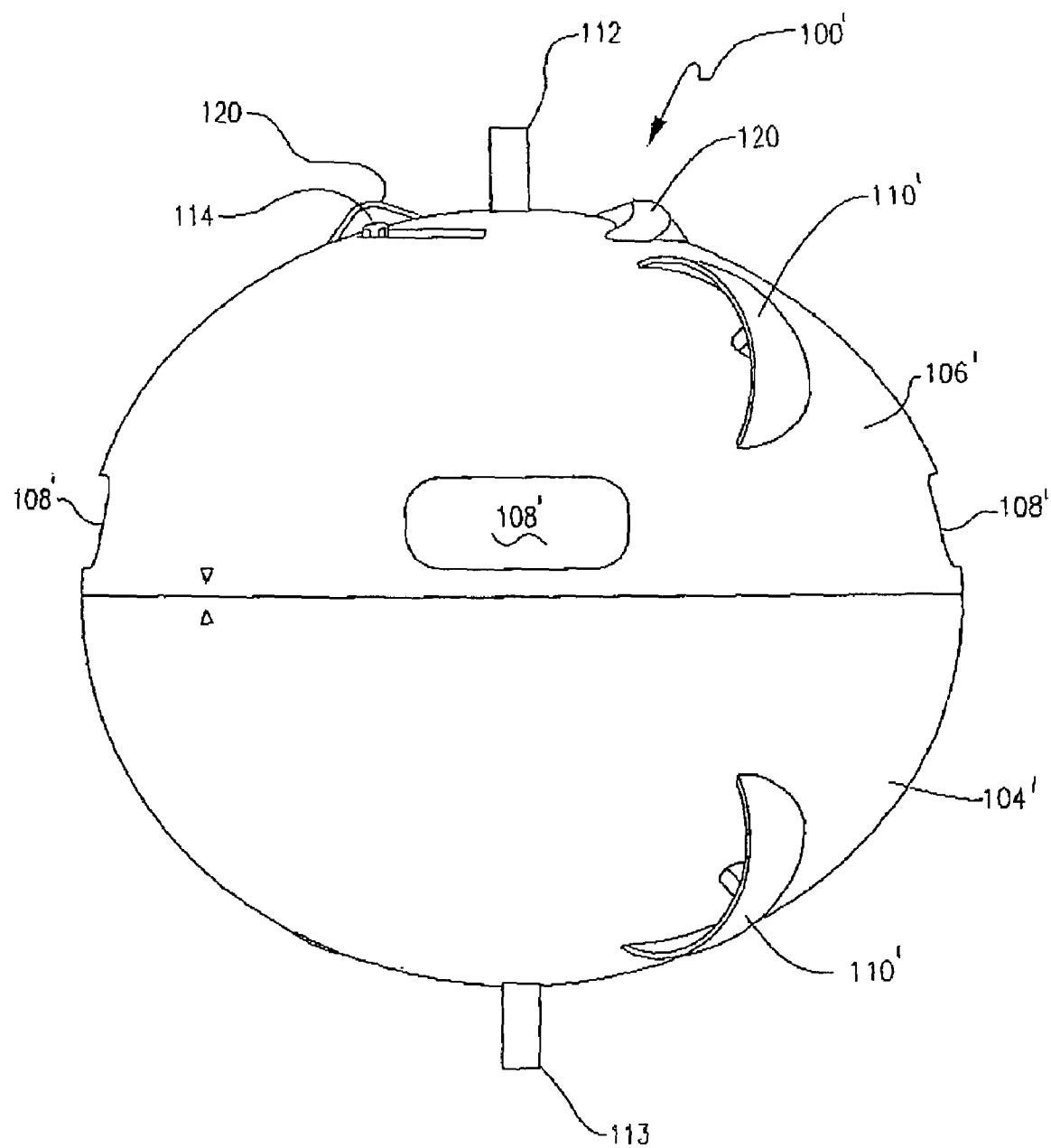
FIG. 3 is a left side elevational view thereof.
Figure 4:
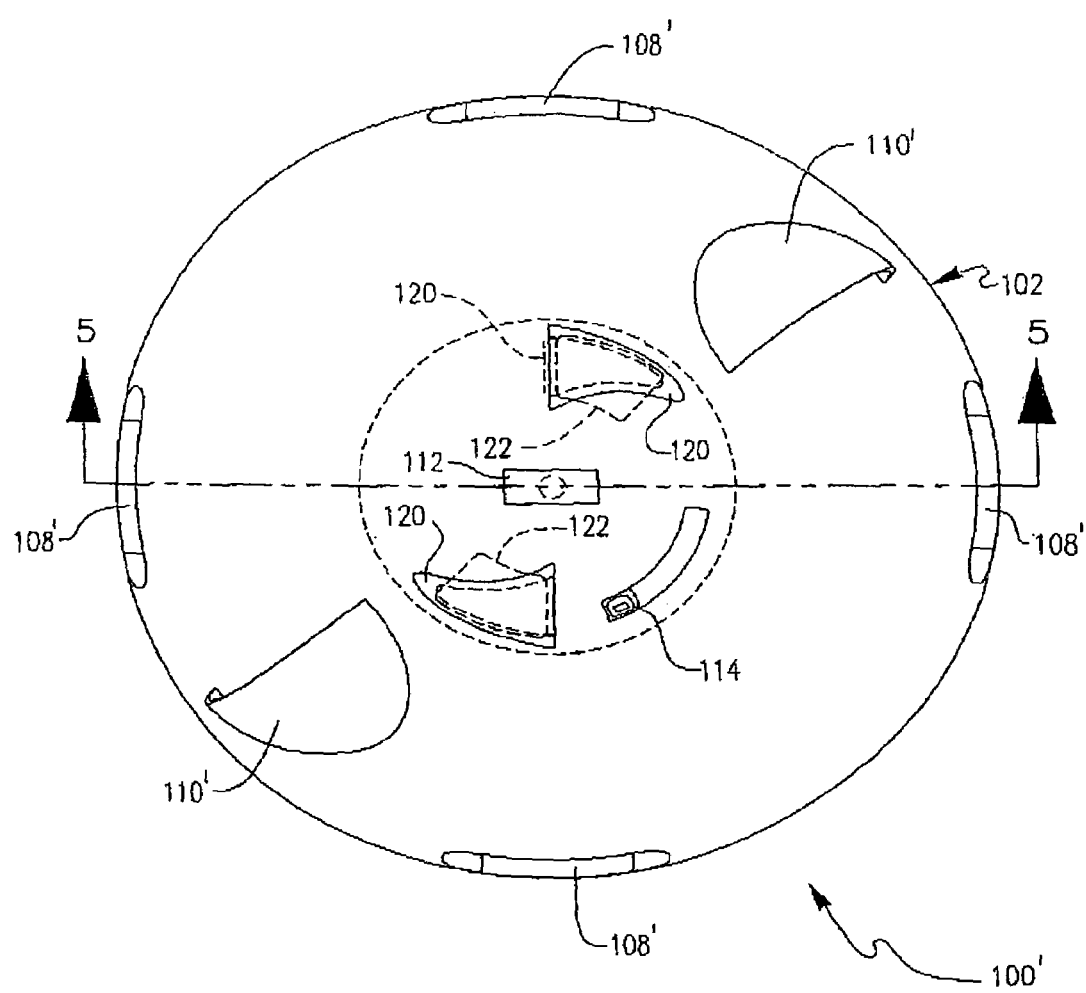
FIG. 4 is a top plan view thereof.
Figure 13:
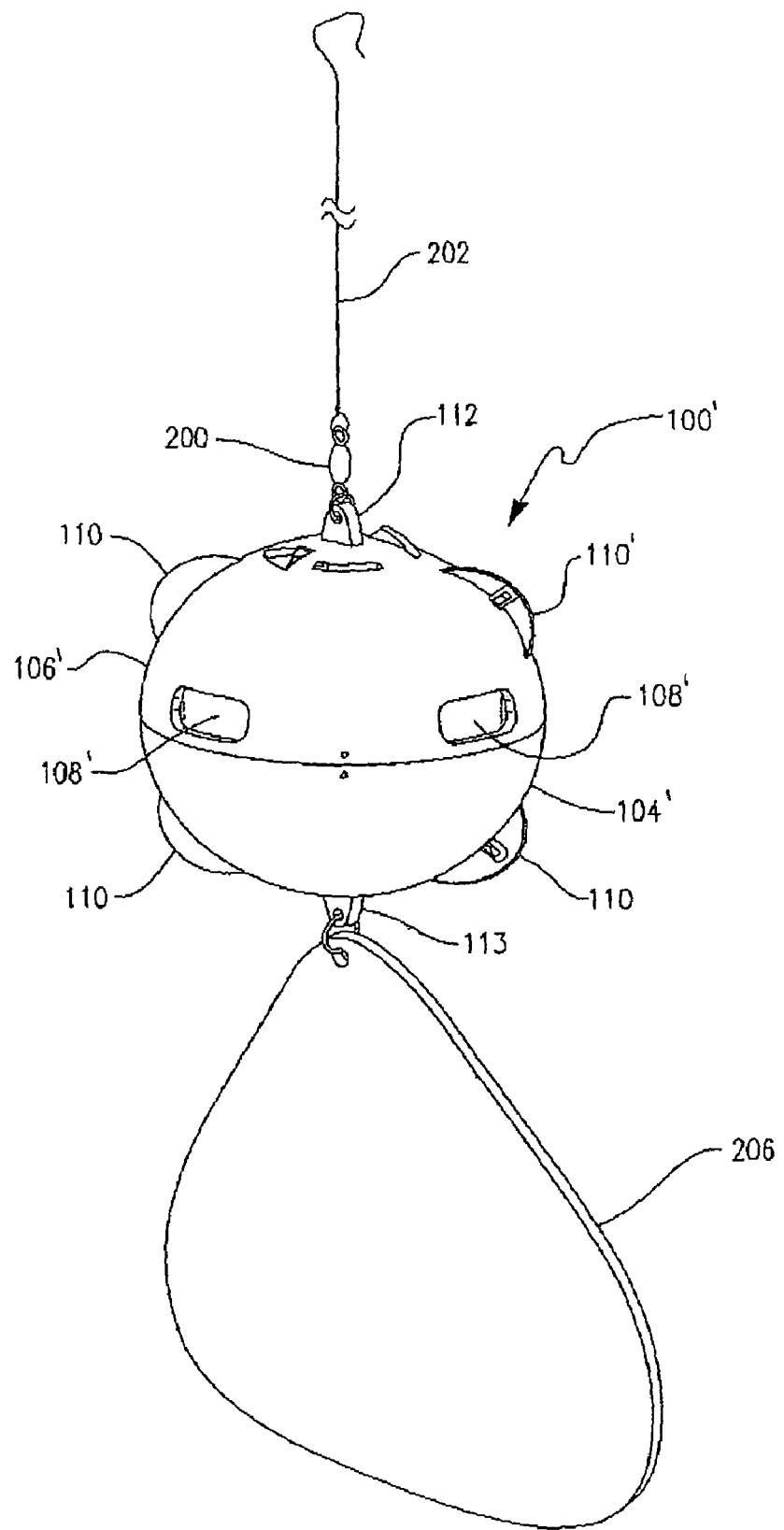
FIG. 13 is a perspective view of a embodiment of FIG. 2 with the addition of a tail element.
Figure 14:
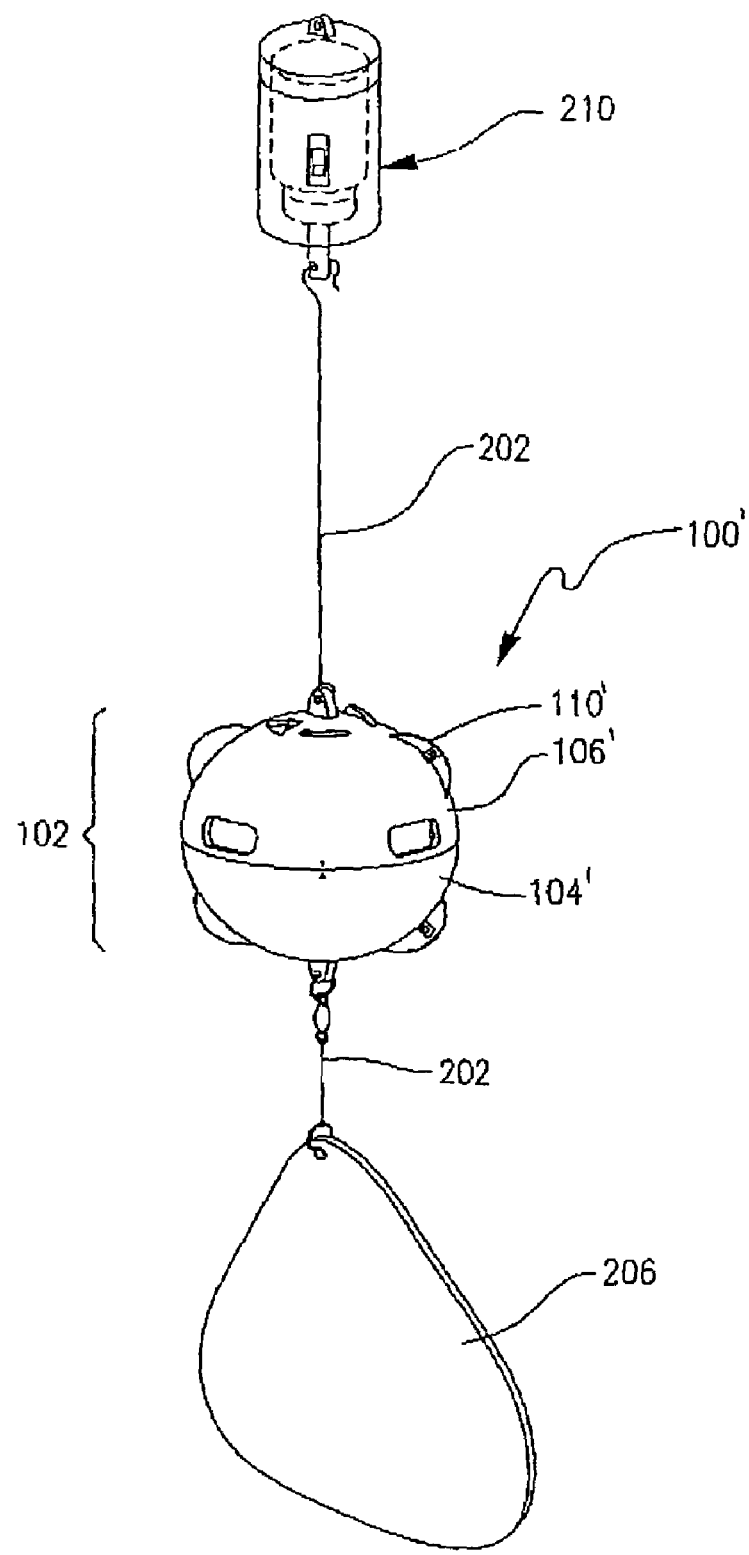
FIG. 14 is a perspective view of a the embodiment of FIG. 13 with the addition of a motor.

An alternate form of the air freshener dispenser apparatus 100' is indicated at FIG. 2. This air freshener dispenser apparatus 100' again has a two-piece container 102 of a top portion 106' and a bottom portion 104', each of a hemisphere shape, which when snapped together form a sphere, with permanently attached wings 110 and that has a hanger 112 from which it may be suspended. Orifices 108' permit the movement of air across the scent carrier element 76 carrying air freshening compounds to exit the air freshener dispenser apparatus 100' and affect the adjacent clothing, sporting equipment of the like neutralizing any odor associated with the clothing, etc. The two-piece container 102 is of plastic or any other moldable, lightweight materials. The top section 106' and the bottom section 104' are interconnected by a sliding self-locking mechanism. The interconnection of the two pieces, 104', 106', creates an internal area in which various contents, such as a scented fragrance disk, stay securely within the spherical container 102. When the air freshener dispenser apparatus 100' is suspended by the hanger 112 these wings 110 allow the sphere to rotate freely with the slightest amount of external airflow. As the spherical container 102 rotates or turns, the scented fragrance disk comprising the scent carrier element 76 within the sphere is naturally dispensed by the centrifugal force generated by the rotation. Vent 120 acts as an air intake vent and permits air flow into the spherical container 102. The amount of air inlet into the vent 120 is controlled by vent control 114. FIG. 3 is a left side view of the air freshener dispenser apparatus 100'. Also shown in both FIGS. 2 & 3 is a bottom hanger 113 permitting the air freshener dispenser apparatus 100' to be hung from either end and to permit other materials, such as the tail 206 as shown in FIGS. 13 & 14 to be suspended. The vent 120 inlets air into the air freshener dispenser apparatus 100' with the vent control extension 122, shown in phantom at FIG. 4, selectively covering some or all of the vent 120. Also shown here in phantom is the vent outline 121. Because the vent 120 extends from the air freshener dispenser apparatus 100', the vent outline 121 indicates the area cut out of the sidewall of air freshener dispenser apparatus 100' under the vent 120. Manually moving the vent control arm 114 pushes the vent control extension 122 to cover the opening formed by vent 120, as shown at FIG. 4. By controlling the amount of air entering air freshener dispenser apparatus 100', a user can control the amount of scented air exiting orifice 108'.

Figure 5:
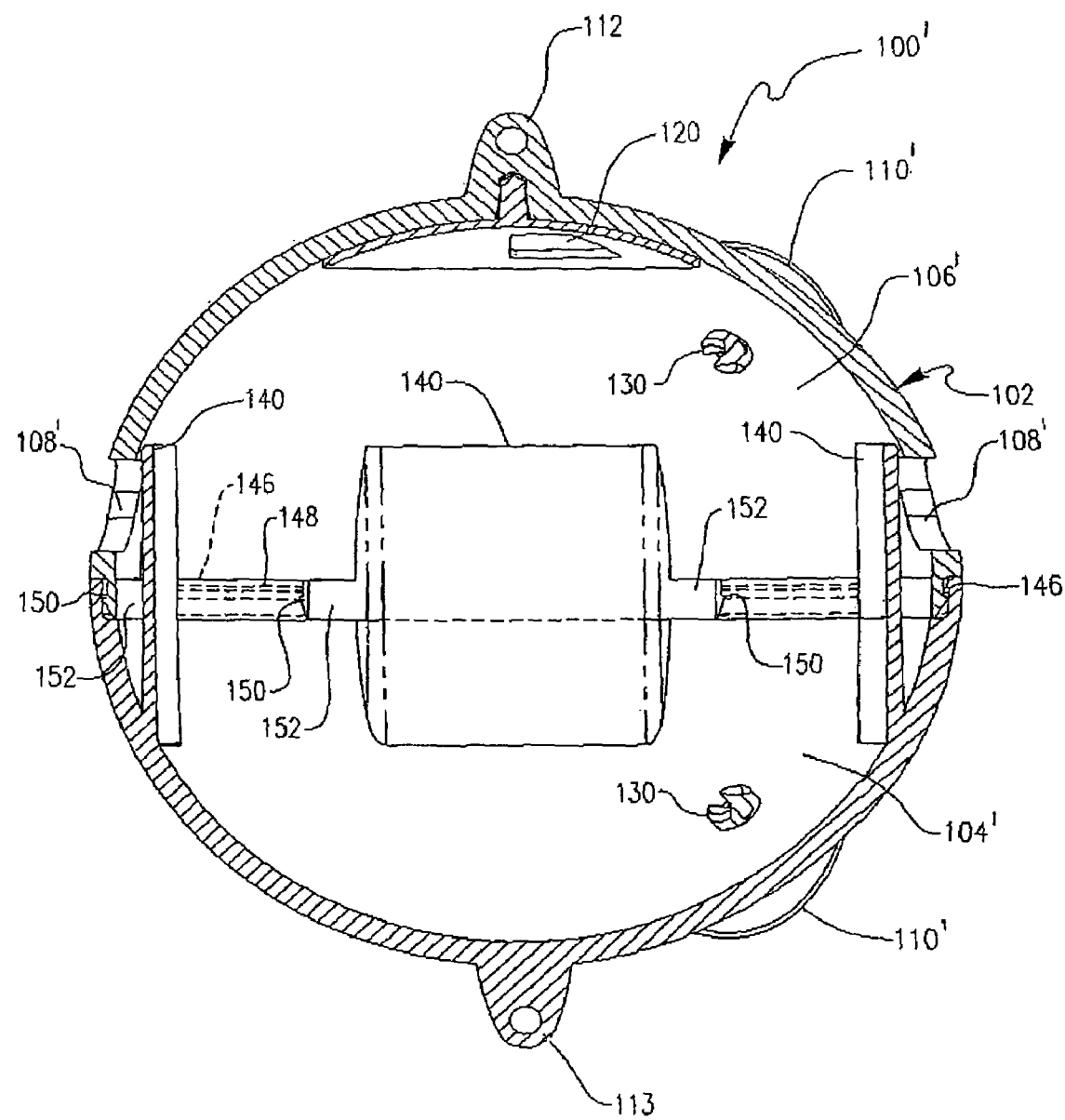
FIG. 5 is a front sectional view taken along the line 4-4 in FIG. 4.

Another form of a two-piece spherical air freshener dispenser apparatus 100' is shown at FIG. 5 which has gates 140 formed into the side walls of bottom portion 104' such that when the top portion 106' is manually snap fit into place on bottom portion 104', forming a sphere, the attachment means permits the bottom portion 104' to be rotated or turned relative to the top portion 106', which moves the gate 140 to selectively open or close the orifice 108' where the air exit's the freshener dispenser apparatus 100'. In this manner, the amount of air flow through the air freshener dispenser apparatus 100' is controlled. Also illustrated at FIG. 5 are wing attachments 130 by which the wings 110' are snap-fit through an aperture formed in the side walls of the spherical container 102. Air flow movement is caught by the wings 110' which cause the hanging air freshener dispenser apparatus 100' when hanging in some means by hanger 112, to turn in the air, releasing scent.

The two-piece air freshener dispenser apparatus 100, 100' utilize attachment means such that when the top section 106' is snap fit onto the bottom section 104', the two portions are slidable relative to each other, as described above, after being snap fit together, such that the gates 140 can be selectively positioned to cover all or part of the orifices 108'. The attachment means which permit the snap fit of the top portion 106' to the bottom portion 104' consist of a ridge 146 formed in the inner sidewall of the top portion 106' which is manually snap fit over a lip 150 formed in the sidewall of the bottom portion 104' permitting the two portions 104', 106' to be snap fit together yet able to be rotated or turned on a horizontal plane relative to each other. This permits the gate 140 to be positioned to cover all or a portion of the orifices 108' limiting air from exiting the spherical container 102. The gate 140 is molded as part of the bottom portion 104'. As shown, the gate 140 is an arcuate shaped structure along the outside edge to follow the curve of the spherical air freshener dispenser apparatus 100' while being generally a square-shaped scoop so as to cover an orifice 108'. The ridge 146 is formed on a ring 148 and molded as part of the top portion 106'. When the ridge 146 is positioned adjacent the lip 150 and is manually pushed past the lip 150 molded as part of an edge 152, the top portion 106' is retained by the bottom portion 104' forming a sphere 102 and the bottom portion is turned relative to the top portion 106'.

Other attachment means are possible to attach the top portion 106' to the bottom portion 104' for forming the sphere 102. Shown at FIG. 6 is an air freshener dispenser apparatus 100" which adds a series of posts 160 formed in the sidewall of the top portion 106' and with hooks 162 formed on the posts 160 that are received by a center portion 170 that is snap fit onto the bottom portion 104' and provides a receiver, an opening 172, formed in the center portion 170 that provides a one-way attachment of the post hook 162 to the center portion 170 mounted on the bottom portion 104'.

Figure 6:
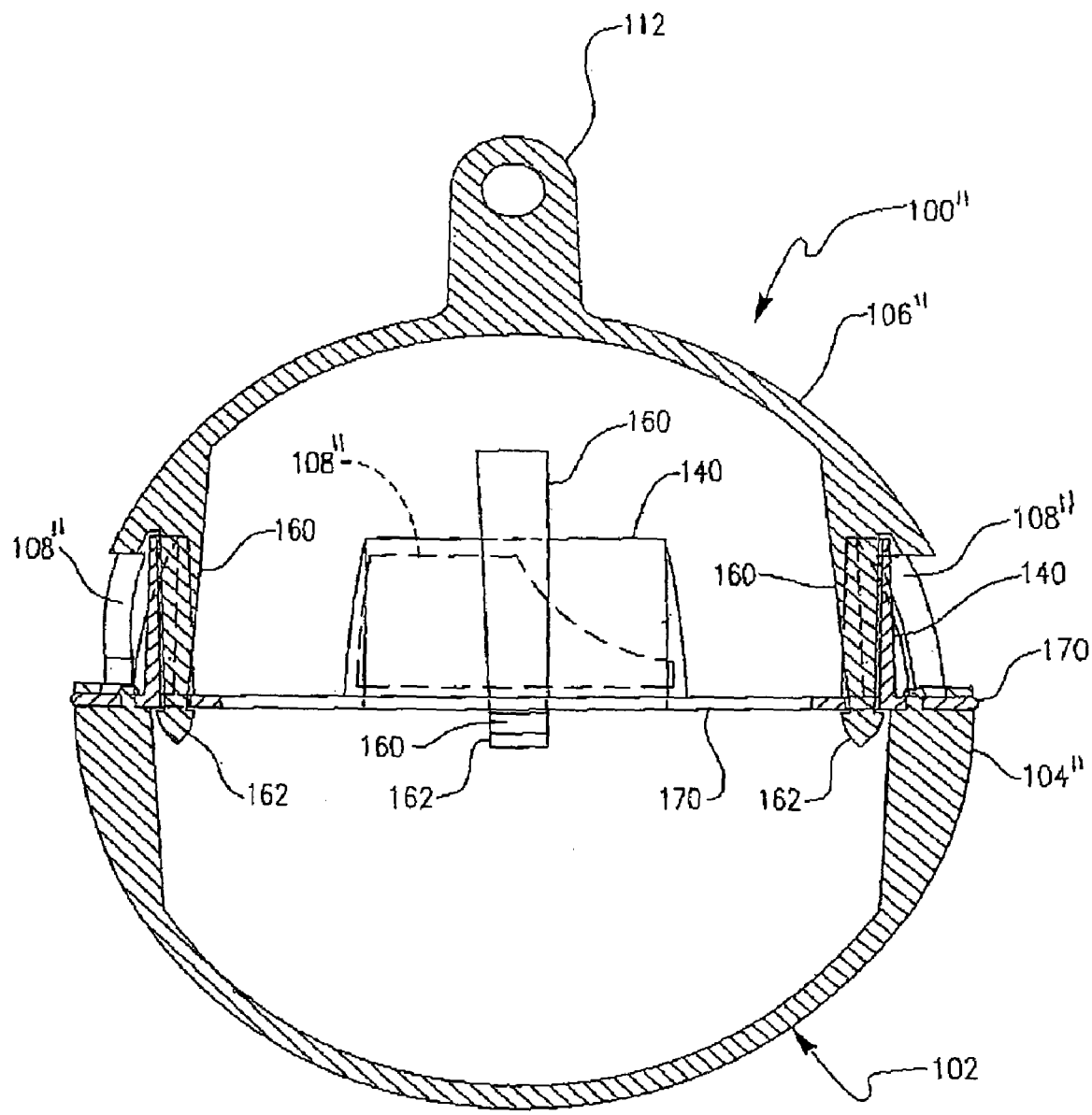
FIG. 6 is a view similar to that of FIG. 5 showing a first alternate form of the invention.
Figure 7:
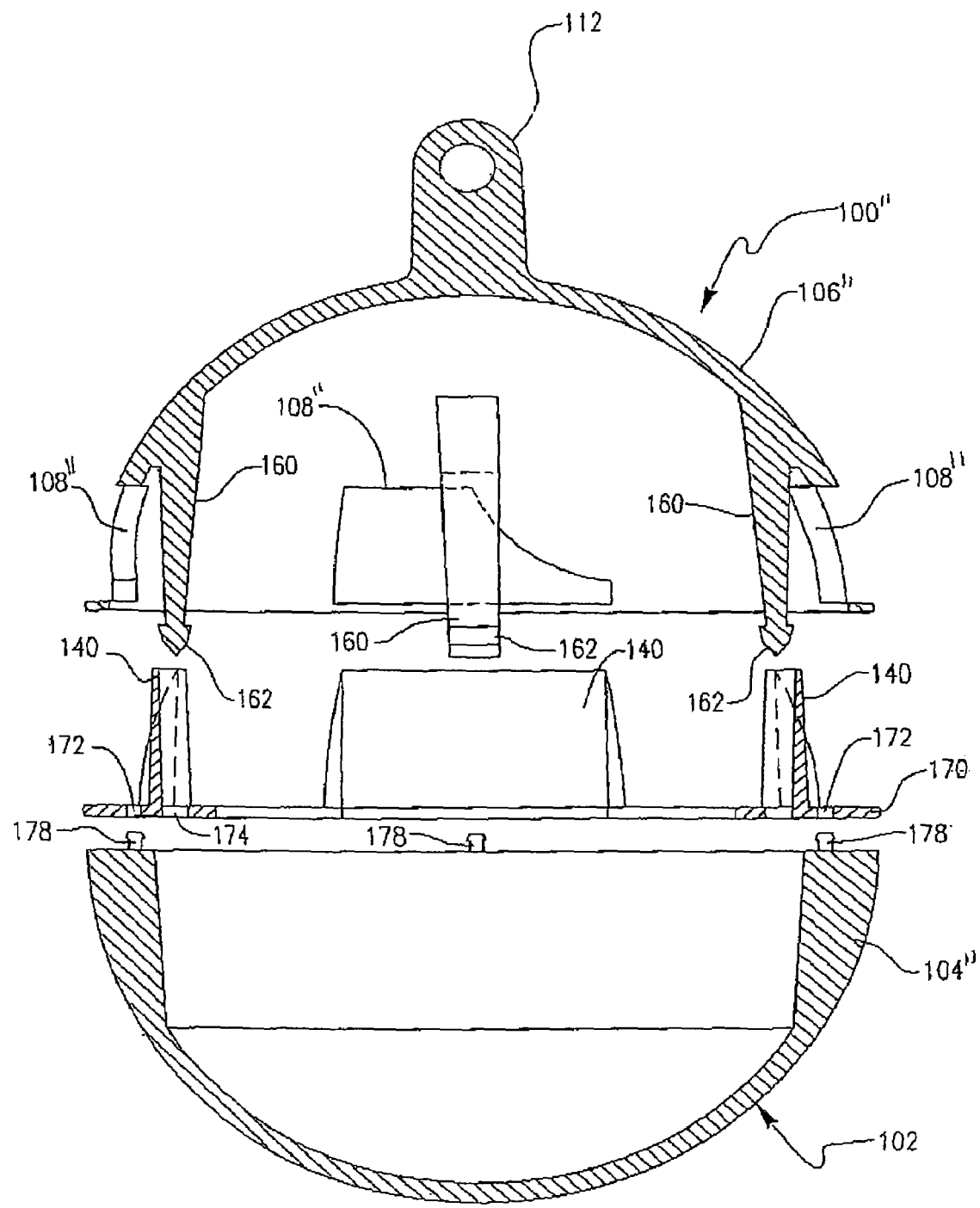
FIG. 7 is an exploded view thereof.

FIG. 7, is an exploded view of the embodiment shown at FIG. 6. The center portion 170 has openings 172 for receiving a series of snap heads 178 molded into bottom portion 104" side wall edge permitting the center portion 170 to be snap fit onto the bottom portion 104". A series of hook slot opening 174 receive the series of hooks 162 formed in the top portion 106" side wall edge and provide a limit to the amount of rotation or turning of the bottom portion 104" relative to the top portion 106". The three piece air freshener dispenser apparatus 100" can be snap fat together with the top portion 106" turns relative to the center portion 170, a slave to the bottom portion 104". Rotation of the top portion 106" relative to the center portion 170 mounted on the bottom portion, 104" the assembly permits the gate 140 to adjustably cover the orifices 108" controlling the amount of air freshener released by the air freshener dispenser apparatus 100".

Figure 8:
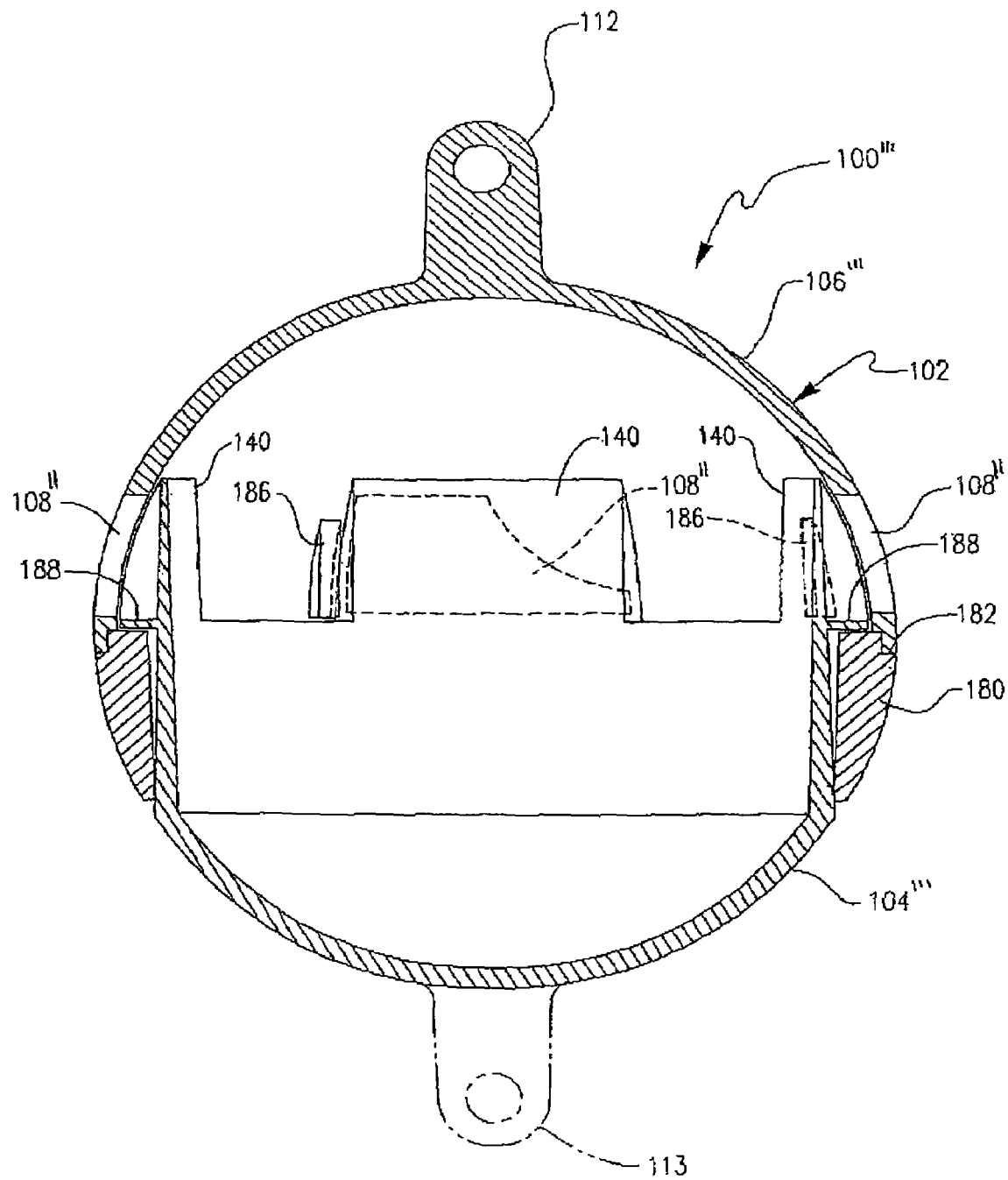
FIG. 8 is a view similar to that of FIG. 6 showing a second alternate form of the invention.
Figure 9:
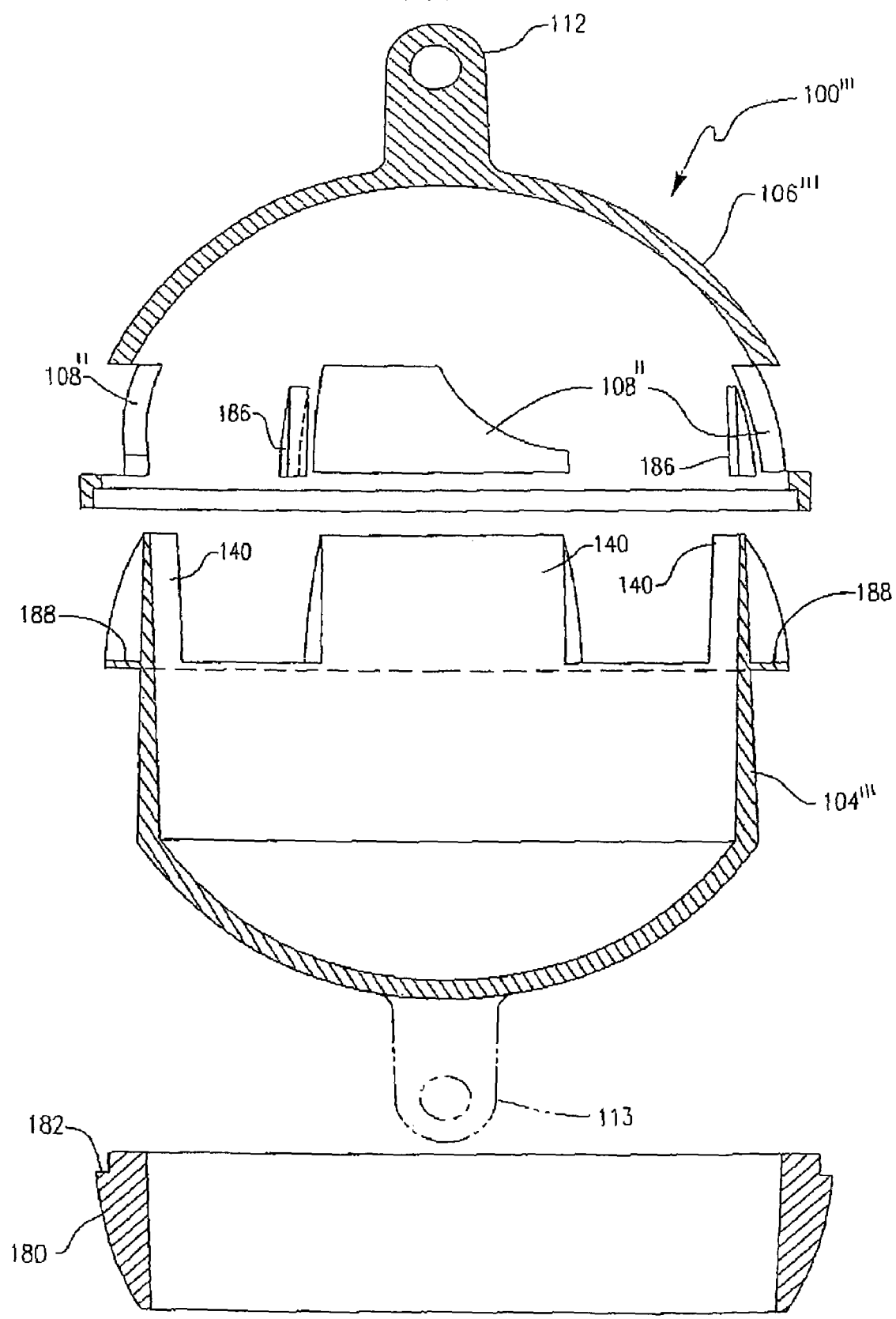
FIG. 9 is an exploded view thereof.

Chemical bonding agents, such as adhesives, can also be used to attach the top portion 106''' to the bottom portion 104''' to form an air freshener dispenser apparatus 100''' such as shown at FIGS. 8 & 9. Here a middle portion 180 has a cut-out 182 that receives the adhesive means attaching the middle portion 180 to the top portion 106''' and provides a shelf 188 on which bottom portion 104''', held in position by affixed middle portion 180, to rotate relative to top portion 106'''. Gate 140 is molded as part of a middle portion 180 shown at FIGS. 8 & 9. Here the top portion 106''' having orifices 108'" formed therein, to top and bottom portions attached to each other by means of a middle portion 180 which acts as a belt to hold the pieces together. Also shown in phantom is a bottom banger 113 which permits other structure to be suspended from air freshener dispenser apparatus 100'''. Again the top portion 106''' and bottom portions when positioned together form a sphere 102 and the top portion 106''' again turns within the assembly such that the orifice 108" of the top portion 106''' may be adjustable covered by the gate 140 formed as part of the bottom portion 104'''.

Figure 10:
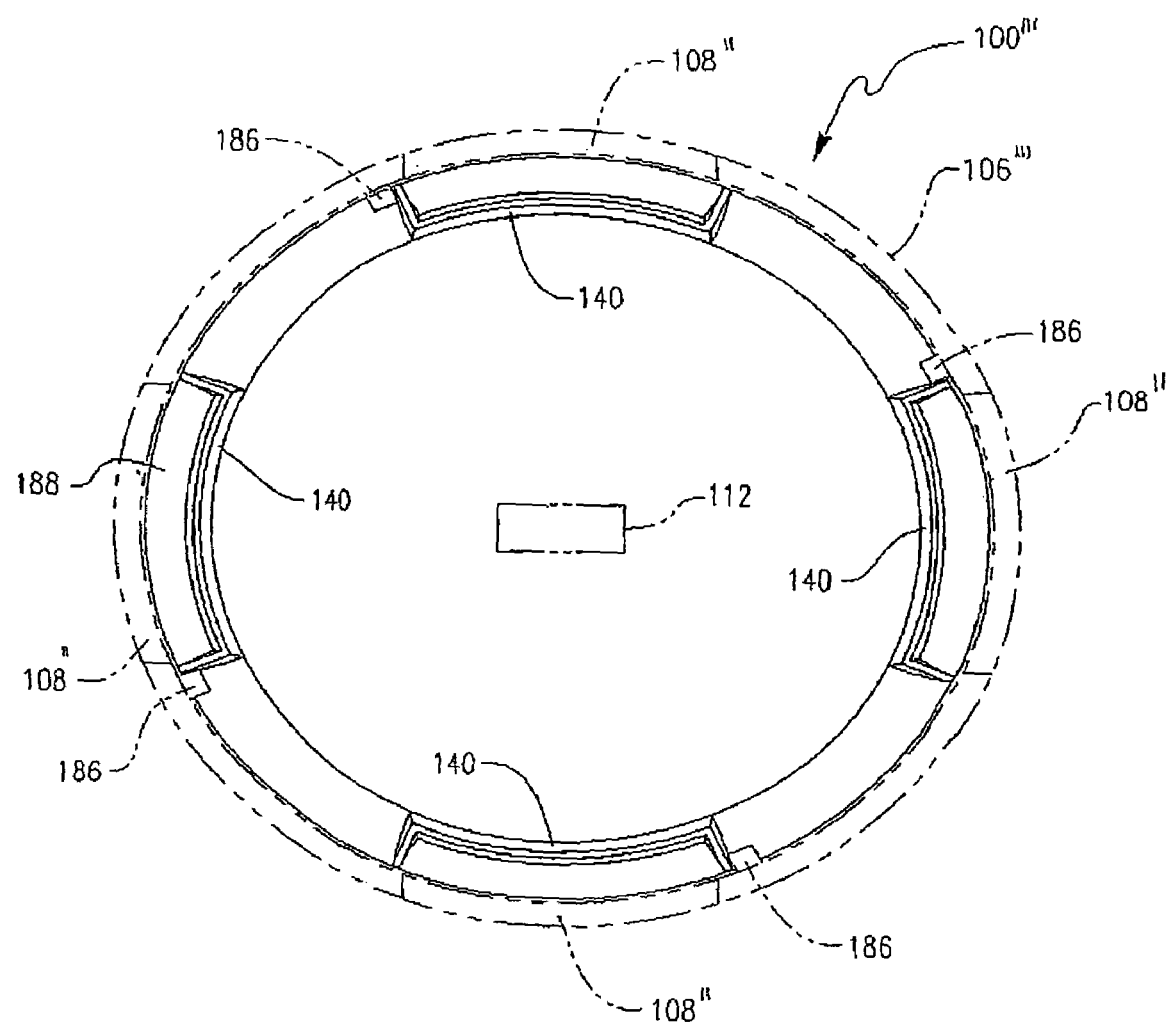
FIG. 10 is a top plan view of the embodiment of FIG. 8 with parts shown in phantom dashed lines.

FIG. 10 is a top plan view of the embodiment of FIGS. 8 & 9 with parts shown in phantom dashed lines. The structure shown here includes a stop 186 that limits the rotation of the bottom portion 104''' relative to the top portion 106'''.

Figure 11:
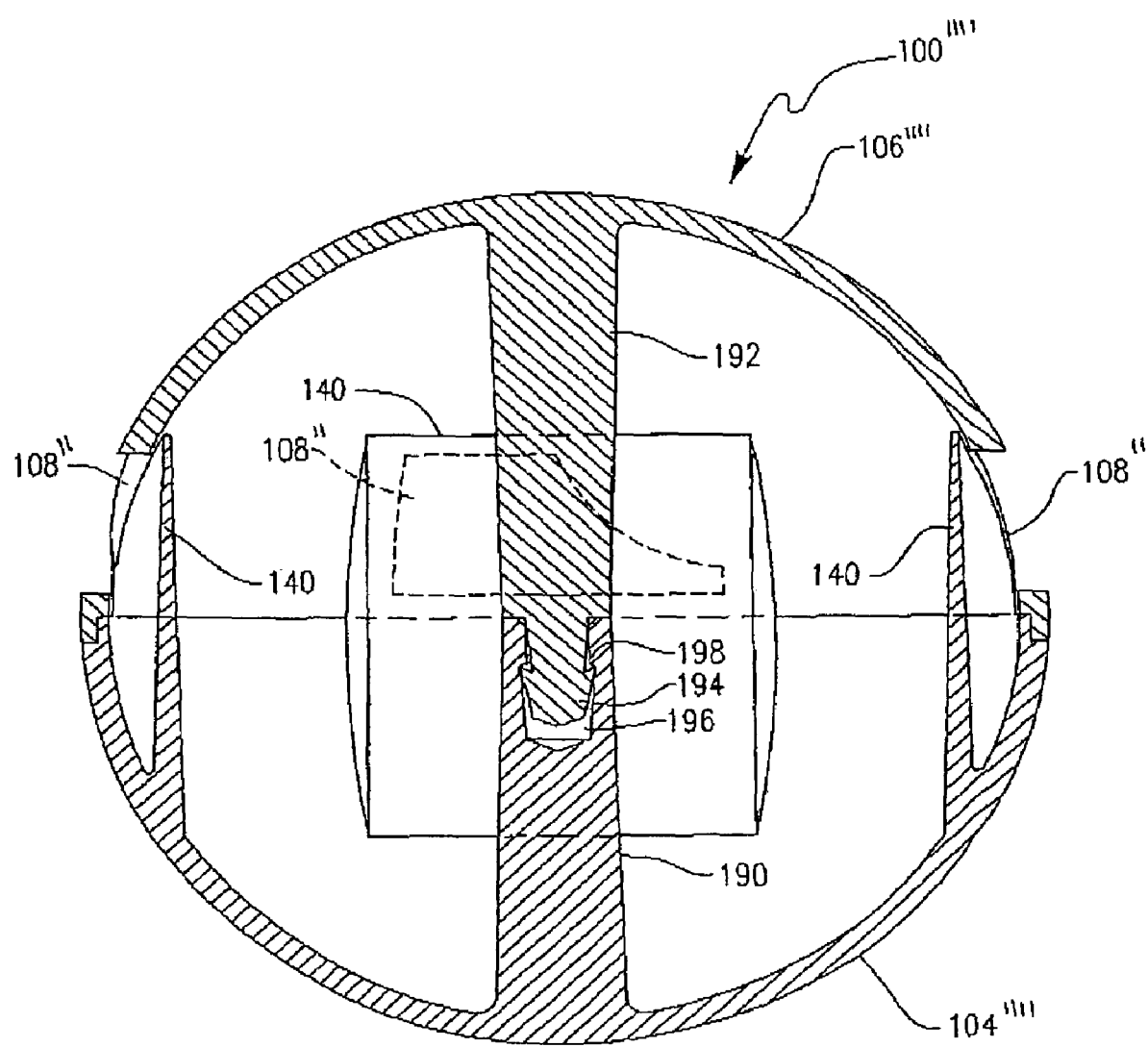
FIG. 11 is a view similar to that of FIG. 7 showing a third alternate embodiment of the invention.

Other attachment means are possible to attach the top portion 106'''' to the bottom portion 104'''' for forming the sphere 102. Shown at FIG. 11 is a two piece air freshener dispenser apparatus 100'''' having a two-piece center post, bottom portion center post 190, and top portion center post 192 with a hook 194 formed in the top portion center post 192 that is received by a female opening a receiver 196 formed in bottom portion center post 190. When manually positioned together, the top portion 106'''' is attached to the bottom portion 104'''' when the hook 194 is manually pushed past a rim 198 of receiver 196 and the hook 194 catches the rim 198. Again, the gate 140 is carried by the bottom portion 104'''' and once the top and bottom portions are attached to form a sphere 102, the gate 140 may be manually rotated to cover all or part of orifice 108" to control the amount of scent released.

Figure 12:
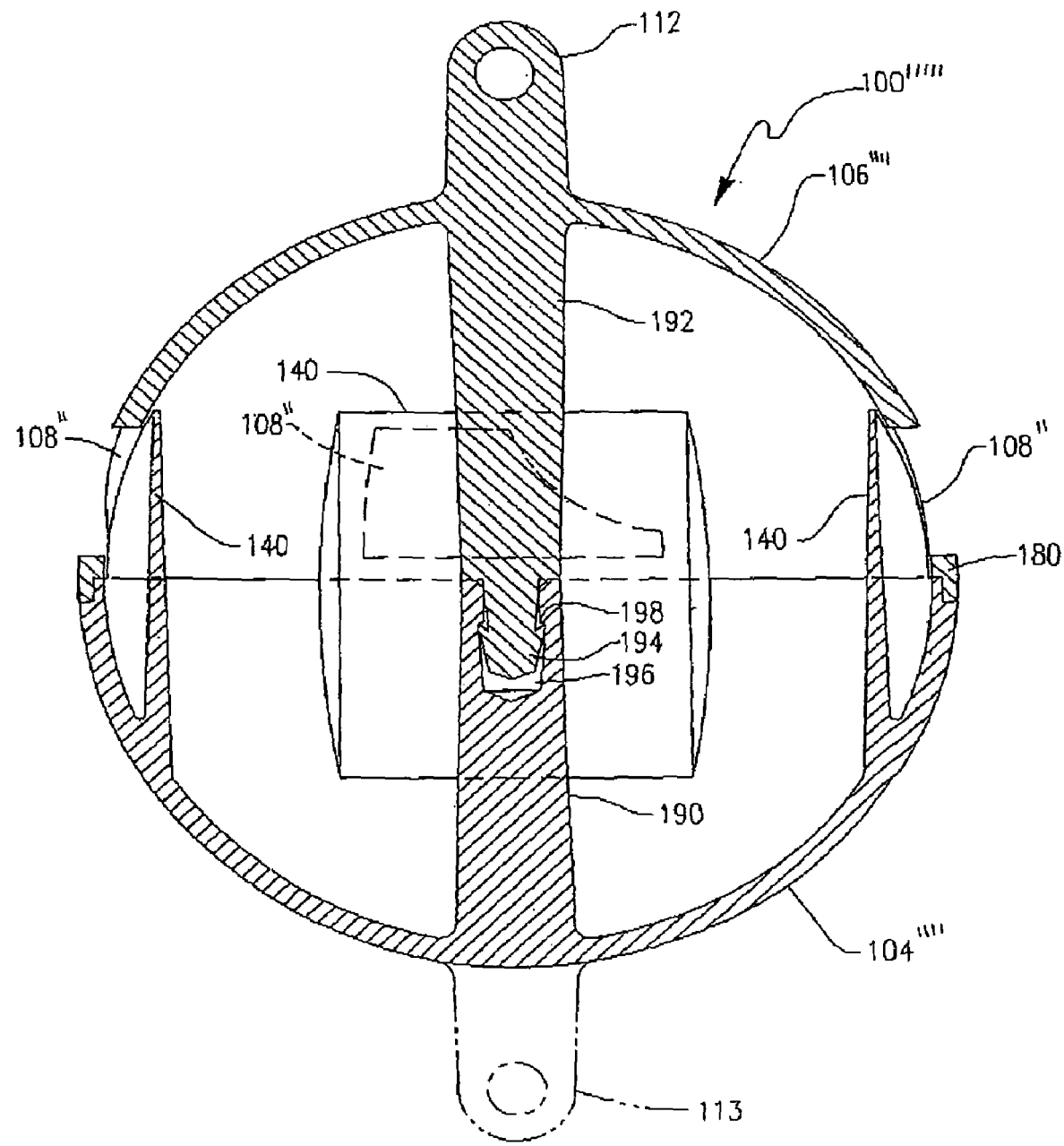
FIG. 12 is a view similar to that of FIG. 10 showing a fourth alternate embodiment of the invention.

FIG. 12 shows an embodiment of the invention, apparatus 100''''', having a center post construction, 190, 192 and a hanger 112.

Any of the spherical container 102 described above can be used to suspend additional structure therefrom, such as a tail 206. FIG. 13 illustrates an embodiment of the invention suspended from the bottom hanger 113 a tail 206, that, because the tail is a slave follower to air freshener dispenser apparatus 100', the tail 206 turns wit the air freshener dispenser apparatus 100' as it turns. The tail 206 can be of two colors, one per side, mimicking a deer tail, e.g. The addition of a deer scent to the aromatic disk 76, held within the spherical container 102, that apparatus becomes a scented lure for use in hunting situations. The deer scent, such as a scent bomb made of actual deer materials, can be absorbed onto a fiber element and inserted within the air freshener dispenser apparatus 100'. The addition of tail 206 which can be set to 'flick' at predetermined intervals by motor 120 which further enhances the air freshener dispenser apparatus 100' for use in hunting situations. FIG. 14 is similar to FIG. 13 in that with the addition of a motor 210 to control the turning of the air freshener dispenser apparatus 100'; results in even dispensing of the air freshener. The motor control can be continuous or pulsating.

Figure 15:
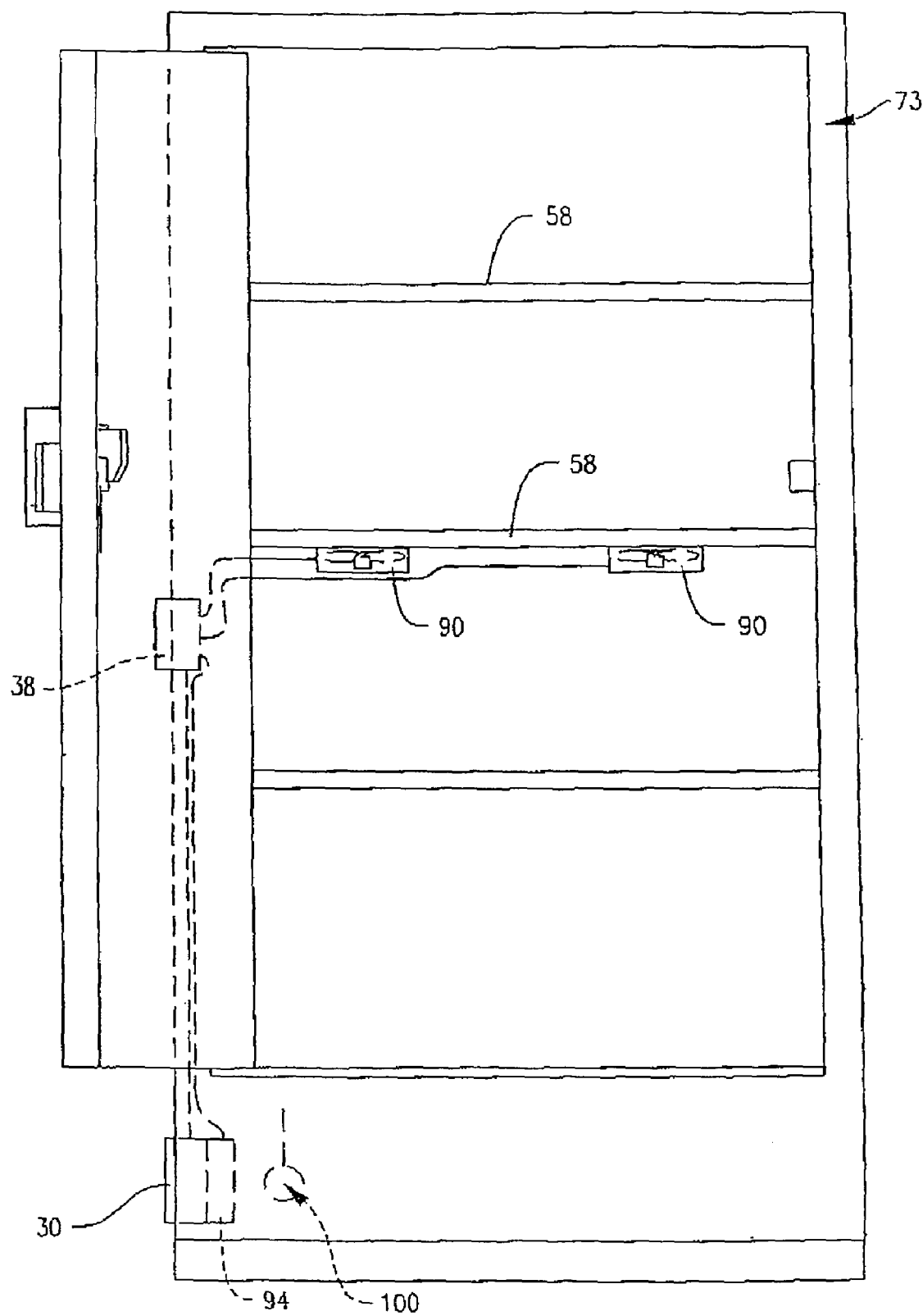
FIG. 15 is a front elevational view of a form of the invention wherein the aromatic structure is shown in a place of use, a specially formed, stand alone, locker with the locker door open.

FIG. 15 is provided to illustrate the invention, apparatus 100, in a place of use, a locker 73 for use in existing lockers or for home use. Shown here is a front cross-sectional view of such a locker with the air freshener dispenser apparatus 100 in place, although it will be understood that any of the embodiments could be used similarly.

Although the present invention has been described in considerable detail with reference to certain preferred embodiments, workers skilled in the art will recognize that changes may be made in form and detail without departing from the spirit and scope of the invention.

What is claimed is:

1. A portable scent dispersion apparatus for use with sports equipment, comprising:

- a two-piece housing having a top and a bottom portion each of which is hemispherical shaped which, when interconnected, has a spherical configuration;
- an aromatic element contained within said housing for dispensing scent;
- means for attaching said top and bottom portions such that said bottom portion is manually rotated relative to said top portion as means for controlling the amount of scent dispensed;
- adjustable orifices, formed in said top portion as means for controlling the amount of scent dispensed wherein said means for attaching said top and bottom portions further comprise a series of posts formed in a sidewall of said top portion, each of said series of posts having a hook formed in an end thereof; and
- a series of hook slot openings formed in a center housing portion snap fit to a sidewall of said bottom housing portion to receive said series of posts as means for attaching said top and bottom portions such that said bottom portion is manually rotated relative to said top portion for positioning a gate, carried by said center housing portion as means for controlling the amount of scent dispensed.

2. A portable scent dispersion apparatus for use with sports equipment, comprising:

- a two-piece housing having a top and a bottom portion each of which is hemispherical shaped which, when interconnected, has a spherical configuration;
- an aromatic element contained within said housing for dispensing scent;
- means for attaching said top and bottom portions such that said bottom portion is manually rotated relative to said top portion as means for controlling the amount of scent dispensed; and
- adjustable orifices, formed in said top portion as means for controlling the amount of scent dispensed wherein said aromatic element further comprises a pair of aromatic discs that are each slit to the center such that they fit perpendicularly relative to each other and rotate within the scent dispersion apparatus.

3. A portable scent dispersion apparatus for use with sports equipment, comprising:

- a two-piece housing having a top and a bottom portion each of which is hemispherical shaped which, when interconnected, has a spherical configuration;
- means for attaching said top and bottom portions such that said bottom portion is manually rotated relative to said top portion;
- an aromatic element contained within said housing for dispensing scent;
- a series of orifices, formed in said top portion; and
- a series of gates formed in said bottom portion, each of said series of gates movable so as to coincide with and movably adjustable relative to each of said series of orifices as means for controlling the amount of scent dispensed;
- said aromatic element further comprises a pair of aromatic discs that are each slit to the center such that they fit perpendicularly relative to each other and rotate within the scent dispersion apparatus.

\* \* \* \* \*

UNITED STATES PATENT AND TRADEMARK OFFICE
CERTIFICATE OF CORRECTION

| | |
|---|---|
| PATENT NO. | : 7,631,814 B2 |
| APPLICATION NO. | : 11/483812 |
| DATED | : December 15, 2009 |
| INVENTOR(S) | : Thomas P. Zarembinski |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this

Second Day of November, 2010

David J. Kappos
*Director of the United States Patent and Trademark Office*